United States Patent
Hsu et al.

(10) Patent No.: US 10,113,970 B2
(45) Date of Patent: Oct. 30, 2018

(54) DETECTION DEVICE

(71) Applicant: NATIONAL TAIWAN UNIVERSITY, Taipei (TW)

(72) Inventors: Cheng-Che Hsu, Taipei (TW); Peng-Kai Kao, Taipei (TW); Min-Chun Chen, Taichung (TW); Po-Wei Yeh, Taichung (TW); Fei-Hung Huang, New Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 15/241,096

(22) Filed: Aug. 19, 2016

(65) Prior Publication Data

US 2017/0052122 A1 Feb. 23, 2017

Related U.S. Application Data

(60) Provisional application No. 62/207,403, filed on Aug. 20, 2015.

(51) Int. Cl.
*G01J 3/30* (2006.01)
*G01N 21/73* (2006.01)

(52) U.S. Cl.
CPC ..... *G01N 21/73* (2013.01); *G01N 2201/0221* (2013.01)

(58) Field of Classification Search
CPC ......... G01N 21/73; G01N 21/68; G01J 3/443; H01J 49/105; H05H 1/30
USPC ....................................................... 356/316
See application file for complete search history.

(56) References Cited

U.S. PATENT DOCUMENTS

| | | |
|---|---|---|
| 4,362,936 A | 12/1982 | Hofmann et al. |
| 5,379,103 A | 1/1995 | Zigler |
| 5,798,832 A | 8/1998 | Hnilica et al. |
| 6,069,695 A | 5/2000 | Rohr et al. |
| 6,359,687 B1 | 3/2002 | Cheng et al. |
| 6,900,734 B2 | 5/2005 | Duan |
| 6,943,879 B2 | 9/2005 | Ukon |
| 7,123,361 B1 | 10/2006 | Doughty |
| 7,273,995 B1 * | 9/2007 | Manz ............... H05H 1/48 219/121.43 |
| 7,417,730 B2 | 8/2008 | Duan et al. |
| 7,460,225 B2 | 12/2008 | Karanassios |
| 7,733,482 B2 | 6/2010 | Ruda et al. |
| 7,875,825 B2 | 1/2011 | Takamura et al. |
| 8,101,923 B2 | 1/2012 | Orlando et al. |
| 8,210,031 B2 | 7/2012 | Jabs et al. |
| 8,436,991 B2 | 5/2013 | Senac |

(Continued)

FOREIGN PATENT DOCUMENTS

| | | |
|---|---|---|
| CN | 104297324 A | 1/2015 |
| CN | 105190302 A | 12/2015 |
| WO | 2015108820 A1 | 7/2015 |

*Primary Examiner* — Md M Rahman
(74) *Attorney, Agent, or Firm* — CKC & Partners Co., Ltd.

(57) ABSTRACT

A detection device, which is used with a mobile electronic device having an image capturing unit, is provided. The detection device includes a plasma generation unit and a light decomposing unit. The plasma generation unit generates plasma from a sample. The light decomposing unit decomposes light emitted by the plasma for spectral analysis. The mobile electronic device receives and analyzes the light decomposed by the light decomposing unit to determine whether an element exist in the sample.

20 Claims, 5 Drawing Sheets

(56) References Cited

U.S. PATENT DOCUMENTS

| | | | |
|---|---|---|---|
| 8,649,006 B2 | 2/2014 | Ardelt et al. | |
| 8,968,286 B2 | 3/2015 | Staack et al. | |
| 9,060,113 B2 | 6/2015 | Rhoads et al. | |
| 9,217,706 B2 | 12/2015 | Mucci et al. | |
| 9,316,540 B1 | 4/2016 | Phua | |
| 2002/0186811 A1* | 12/2002 | Weiss | G01N 23/223 378/6 |
| 2003/0012718 A1* | 1/2003 | Josephson | B01D 53/68 423/241 |
| 2003/0218745 A1* | 11/2003 | Benicewicz | G01N 21/718 356/318 |
| 2004/0099282 A1* | 5/2004 | Kambara | C23C 14/564 134/1.1 |
| 2006/0279732 A1 | 12/2006 | Wang et al. | |

\* cited by examiner

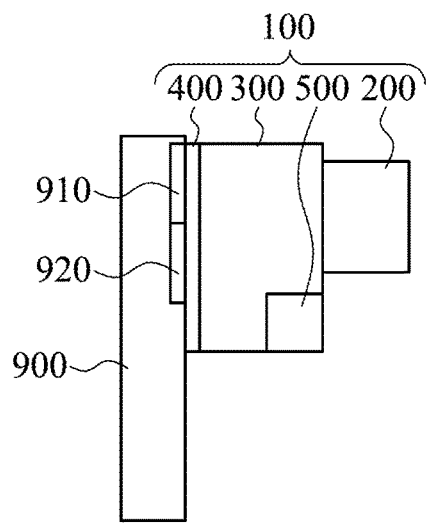
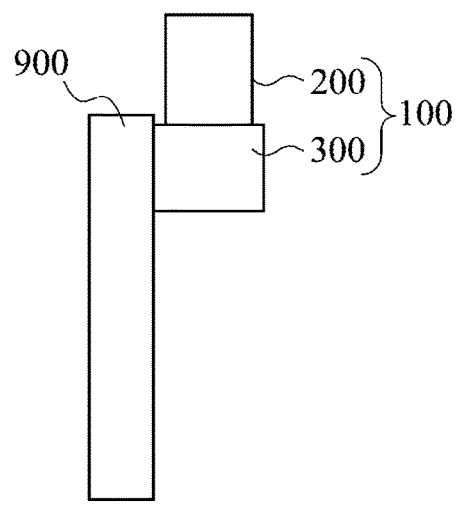
Fig. 2
Fig. 3
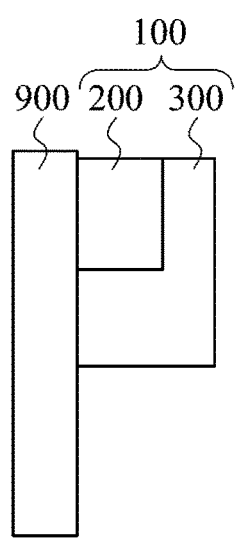
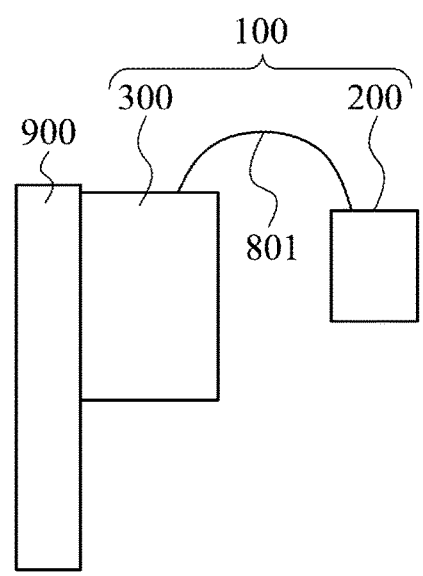
Fig. 4
Fig. 5

DETECTION DEVICE

RELATED APPLICATIONS

This application claims priority to U.S. Provisional Application Ser. No. 62/207,403, filed Aug. 20, 2015, which is herein incorporated by reference.

BACKGROUND

Technical Field

The present disclosure relates to a detection device.

Description of Related Art

Air pollution and water contamination may cause many problems. For example, drinking water with high levels of heavy metal ions over a long period of time may result in health problems such as kidney damage, and many standard about levels of heavy metal ions in drinking water are therefore established. For example, the World Health Organization (WHO) establishes a maximum level of 6 ppb for mercury(II) in drinking water. When routine monitoring indicates that heavy metal levels are above the standard, a water supplier must take steps to reduce the amount of the heavy metal so that is below that level. Water suppliers must notify their customers as soon as practical. Additional actions, such as providing alternative drinking water supplies, may be required to prevent serious risks to public health.

SUMMARY

This disclosure provides a device cooperated with a mobile electronic device to detect a variety of kinds of elements with high sensitivity and to reduce the manufacturing cost of the device.

In one aspect of the disclosure, a device, which is used with a mobile electronic device having an image capturing unit, is provided. The device includes a plasma generation unit and a light decomposing unit. The plasma generation unit generates plasma from a sample. The light decomposing unit decomposes light emitted by the plasma for spectral analysis. The mobile electronic device receives and analyzes the light decomposed by the light decomposing unit to determine whether an element exists in the sample.

In one or more embodiments, the device further includes a fixing member fixing the device to the mobile electronic device.

In one or more embodiments, the plasma generation unit includes a first electrode and a second electrode, and the sample is located between the first electrode and the second electrode.

In one or more embodiments, the plasma generation unit further includes a plasma generation unit housing forming a space. The first electrode and the second electrode are disposed in the space, and the sample is an air in the space.

In one or more embodiments, the plasma generation unit further includes a liquid-absorbing member. The liquid-absorbing member is disposed on the first electrode. The sample is a liquid in the liquid-absorbing member.

In one or more embodiments, the second electrode is disposed above the first electrode.

In one or more embodiments, the first electrode is disposed above the second electrode.

In one or more embodiments, the liquid-absorbing member is made of a filter paper, a fabric, or a porous material.

In one or more embodiments, the liquid-absorbing member is attached to the first electrode, and the first electrode is a negative electrode.

In one or more embodiments, the first electrode has an opening, and the opening is a slit or a pinhole.

In one or more embodiments, the second electrode is a pin.

In one or more embodiments, the plasma generation unit includes a first electrode, a second electrode, and a liquid-absorbing member. The liquid-absorbing member is disposed on the first electrode, and the sample is a liquid in the liquid-absorbing member. The second electrode is not disposed directly above the liquid-absorbing member.

In one or more embodiments, the light decomposing unit includes a light dispersive member decomposing the light emitted by the plasma.

In one or more embodiments, the light dispersive member is a prism or a grating.

In one or more embodiments, the light decomposing unit includes a light decomposing unit housing, and the light decomposing unit housing has an opening receiving the light emitted by the plasma.

In one or more embodiments, the opening is a pinhole or a slit.

In one or more embodiments, the light decomposing unit further includes a light blocking structure blocking a zeroth order diffraction part of light passing the opening.

In one or more embodiments, the light blocking structure is integrally formed on the light decomposing unit housing.

In one or more embodiments, the device further includes a switch control unit controlling the time period between the turn-on time ofthe plasma generation unit and the turn-on time of the image capturing unit of the mobile electronic device.

In another aspect of the disclosure, a device is provided. The device includes a fixing member, a plasma generation unit, and a light decomposing unit. The fixing member fixes the device to a mobile electronic device. The plasma generation unit generates plasma from a sample. The light decomposing unit decomposes light emitted by the plasma for spectral analysis. The mobile electronic device receives and analyzes the light decomposed by the light decomposing unit to determine whether an element exists in the sample.

The device cooperated with a mobile electronic device detects whether an element exists in the sample by spectral analysis of the plasma generated from the sample, so the device can detect a variety of kinds of elements with high sensitivity. In addition, since the device is used with the mobile electronic device, the device does not need to include the image capturing unit and the data processing unit. Therefore, the manufacturing cost of the device can be reduced. Finally, the plasma generation unit and the light decomposing unit can be manufactured in small sizes, so the device is portable. Therefore, it is very convenient to detect whether an element exists in the sample by using the device.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiment, with reference made to the accompanying drawings as follows:

FIG. 2 is a schematic side view of the detection device and the mobile electronic device according to one embodiment of this disclosure;

FIG. 3 is a schematic side view of the detection device and the mobile electronic device according to another embodiment of this disclosure;

FIG. 4 is a schematic side view of the detection device and the mobile electronic device according to another embodiment of this disclosure;

FIG. 5 is a schematic side view of the detection device and the mobile electronic device according to another embodiment of this disclosure;

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically depicted in order to simplify the drawings.

Figure 1:
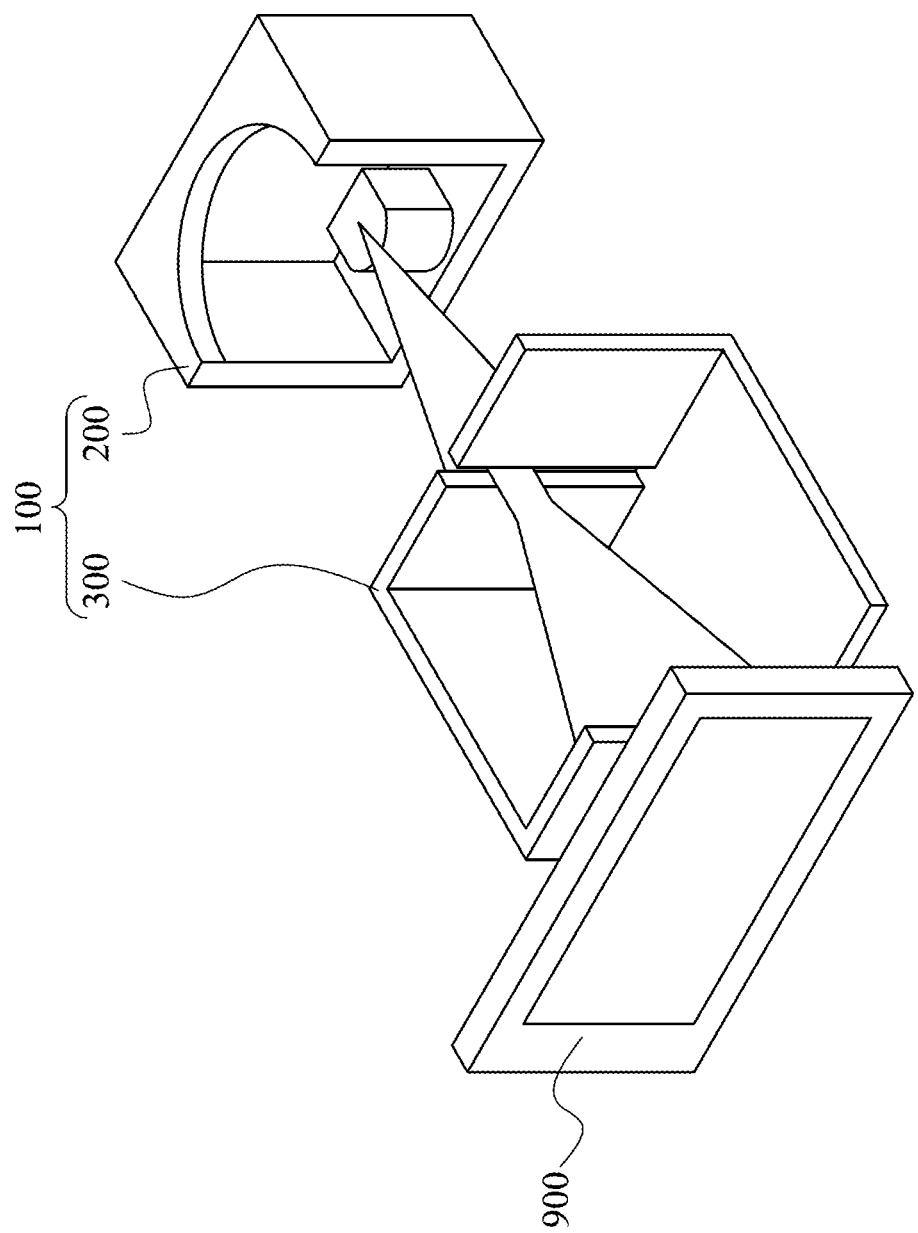
FIG. 1 is a schematic perspective view of a detection device and a mobile electronic device according to one embodiment of this disclosure.

FIG. 1 is a schematic perspective view of a detection device 100 according to one embodiment of this disclosure. A detection device 100 is provided. The detection device 100 is mainly cooperated with a mobile electronic device 900 to detect whether an element, for example, heavy metal ions, exists in the sample.

As shown in FIG. 1, the detection device 100 is used with a mobile electronic device 900. The detection device 100 includes a plasma generation unit 200 and a light decomposing unit 300. The plasma generation unit 200 generates plasma from a sample. The light decomposing unit 300 decomposes light emitted by the plasma for spectral analysis. The mobile electronic device 900 receives and analyzes the light decomposed by the light decomposing unit to determine whether an element exists in the sample.

FIG. 2 is a schematic side view of the detection device 100 and the mobile electronic device 900 according to one embodiment of this disclosure. As shown in FIG. 2, the mobile electronic device 900 includes an image capturing unit 910. The mobile electronic device 900 may be a smartphone or a tablet.

The image capturing unit 910 can include lens, a shutter, a body, and a sensor. The detailed structure of the configuration will not be described here. The sensor may be a CCD (charge-coupled device) or a CMOS (complementary metal-oxide-semiconductor). Embodiments of this disclosure are not limited thereto. The person having ordinary skill in the art can make proper modifications to the sensor depending on the actual application.

The detection device 100 is cooperated with the mobile electronic device 900 to detect whether an element exists in the sample by spectral analysis of the plasma generated from the sample, so the detection device 100 with the mobile electronic device 900 can detect a variety of kinds of elements with high sensitivity.

In addition, the detection device 100 is used with the mobile electronic device 900, in most cases, the customer does not need to additionally buy the mobile electronic device 900 (e.g. the smartphone or the tablet), which already includes the image capturing unit 910 and the data processing unit 920. The functions of the image capturing unit 910 and the data processing unit 920 can be performed by the mobile electronic device 900. Therefore, the detection device 100 does not need to include the image capturing unit and the data processing unit. As a result, the manufacturing cost of the detection device 100 can be reduced. In most cases, the manufacturing costs of the image capturing unit and the data processing unit are much higher than the manufacturing costs of the plasma generation unit and the light decomposing unit. Since the detection device 100 does not include the image capturing unit and the data processing unit, the manufacturing cost of the detection device 100 can be effectively reduced.

Since the price of the detection device 100 becomes much lower due to the reduced manufacturing cost, and the mobile electronic device 900 is a common device in customer's daily life, the detection device 100 becomes very appealing to the customer.

Furthermore, the plasma generation unit 200 and the light decomposing unit 300 can be manufactured in small sizes, so the detection device 100 is portable. When the detection device 100 is used with the mobile electronic device 900, the combined structure of the detection device 100 and the mobile electronic device 900 are still portable. Therefore, it is very convenient to detect whether an element exists in the sample by using the detection device 100.

The detection device 100 further includes a fixing member 400. The fixing member 400 fixes the detection device 100 to the mobile electronic device 900. In some embodiment, the fixing member 400 may be a slot, and the mobile electronic device 900 is assembled in the fixing member 400. In some embodiment, the fixing member 400 may be a clamp, and the mobile electronic device 900 is clamped by the fixing member 400. In some embodiments, the fixing member 400 may be an adhesive layer, and the fixing member 400 can be adhered to the mobile electronic device 900, such that the detection device 100 is fixed to the mobile electronic device 900.

In some embodiments, the detection device 100 may further include at least one optical fiber, at least one lens, and/or at least one mirror. The optical fiber, lens, and/or mirror are disposed between the light decomposing unit 300 and the plasma generation unit 200, such that the light path of the light generated from the plasma generation unit 200 to the light discomposing unit 300 can be adjusted according to the design requirements.

In some embodiments, the plasma generation unit 200 is disposed on one side of the light decomposing unit 300 opposite to the mobile electronic device 900. Embodiments of this disclosure are not limited thereto. FIG. 3 is a schematic side view of the detection device 100 and the mobile electronic device 900 according to another embodiment of this disclosure. As shown in FIG. 3, the plasma generation unit 200 is disposed on the top surface of the light decomposing unit 300. FIG. 4 is a schematic side view of the detection device 100 and the mobile electronic device 900 according to another embodiment of this disclosure. As shown in FIG. 4, the plasma generation unit 200 is embedded in the light decomposing unit 300. FIG. 5 is a schematic side view of the detection device 100 and the mobile electronic device 900 according to another embodiment of this disclosure. As shown in FIG. 5, the plasma generation unit 200 and the light decomposing unit 300 are separate components. The detection device 100 further includes an optical fiber 801, and the optical fiber 801 connects the plasma generation unit 200 and the light decomposing unit 300.

Figure 6:
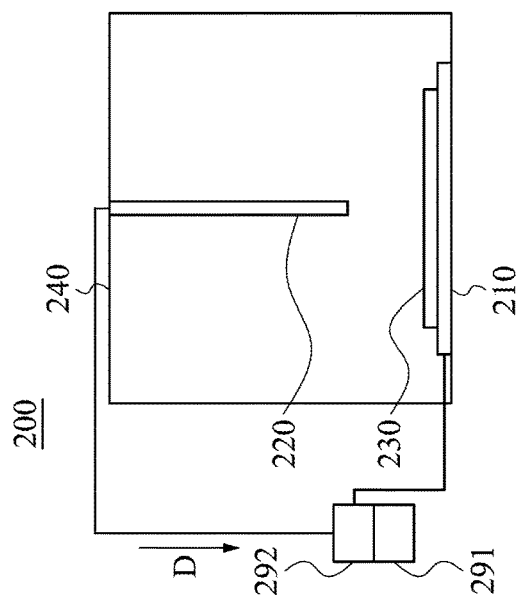
FIG. 6 is a schematic cross-sectional view of a plasma generation unit according to one embodiment of this disclosure.

FIG. 6 is a schematic cross-sectional view of the plasma generation unit 200 according to one embodiment of this disclosure. As shown in FIG. 6, the plasma generation unit 200 includes a first electrode 210 and a second electrode 220, and the sample is located between the first electrode 210 and the second electrode 220. In some embodiments, the plasma generation unit 200 further includes a liquid-absorbing member 230. The liquid-absorbing member 230 is disposed on the first electrode 210. The sample is a liquid in the liquid-absorbing member 230. The second electrode 220 is disposed above the first electrode 210 (the downward direction D is defined by the direction of gravity).

The liquid-absorbing member 230 may be made of a filter paper, a fabric, or a porous material. Embodiments of this disclosure are not limited thereto. The person having ordinary skill in the art can make proper modifications to the liquid-absorbing member 230 depending on the actual application.

The second electrode 220 may be a pin. Embodiments of this disclosure are not limited thereto. The person having ordinary skill in the art can make proper modifications to the second electrode 220 depending on the actual application.

The distance between the first electrode 210 and the second electrode 220 may be less than about 2 mm. In some embodiments, the distance between the first electrode 210 and the second electrode 220 may be in a range from 0.8 mm to 1.2 mm. Embodiments of this disclosure are not limited thereto. The person having ordinary skill in the art can make proper modifications to the distance between the first electrode 210 and the second electrode 220 depending on the actual application.

The plasma generation unit 200 further includes a plasma generation unit housing 240. The first electrode 210 and the second electrode 220 are disposed in the plasma generation unit housing 240. The plasma generation unit housing 240 has a first opening (not shown in Figs), and the light emitted by the plasma can leave the plasma generation unit housing 240 through the first opening. In addition, the plasma generation unit housing 240 does not form a hermetic space, so the air pressure in the plasma generation unit housing 240 is about 1 atm. Embodiments of this disclosure are not limited thereto. In some embodiment, the first opening may be replaced by a transparent portion, and the first transparent portion may be made of, for example, glass.

The plasma generation unit 200 may further include a power supply 291 and a voltage boost module 292. The power supply 291 is electrically connected to the voltage boost module 292. The voltage boost module 292 is electrically connected to the first electrode 210 and the second electrode 220. In some embodiment, the power supply 291 is a direct current power supply, and the output voltage of the power supply 291 is in a range from about 1 volt to about 100 volts. Alternatively, the output voltage of the power supply 291 may be, for example, 9 volts. The voltage boost module 292 is a high-voltage pulsed module, a high-voltage direct current module, or a high-voltage alternating current module, and the output voltage of the voltage boost supply 292 is in a range from about 500 volts to about 10000 volts. Alternatively, the output voltage of the voltage boost supply 292 may be, for example, 3000 volts.

In some embodiments, the power supply 291 may be a battery. In some other embodiments, the plasma generation unit 200 does not include the power supply 291, and the voltage boost module 292 is electrically connected to the mobile electronic device 900. The voltage boost module 292 may be electrically connected to the mobile electronic device 900 through the USB port or the earphone jack of the mobile electronic device 900.

When the plasma generation unit 200 is turned on, there will be a voltage difference between the first electrode 210 and the second electrode 220. The plasma is therefore generated from the air between the first electrode 210 and the second electrode 220. Then, the temperature between the first electrode 210 and the second electrode 220 will rise due to the formation of the plasma, and some of the sample will evaporate into air. Then, some of evaporated sample will become plasma and the plasma will contain species from the sample.

The first electrode 210 is a cathode, and the second electrode 220 is an anode. In some embodiment, the first electrode 210 is a negative electrode, and the second electrode 220 is a positive electrode. Since the liquid-absorbing member 230 is attached to the first electrode 210, and the first electrode 210 is a negative electrode, positive ions generated from the sample will be attracted to the first electrode 210. The first electrode 210 is more heated and more species absorbed in the liquid-absorbing member 230 will evaporate. Therefore, the light emission intensity of the plasma from the species absorbed in the liquid-absorbing member 230 becomes stronger.

Figure 7:
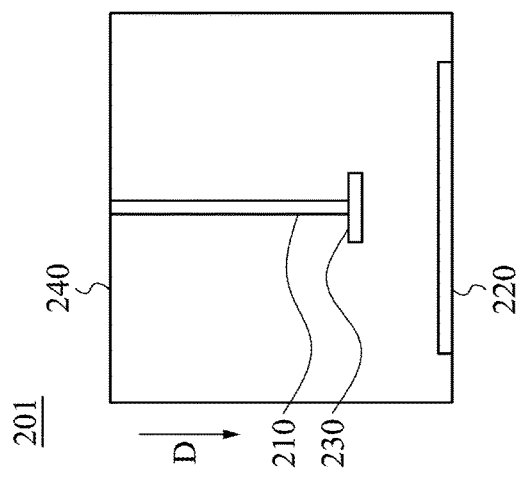
FIG. 7 is a schematic cross-sectional view of the plasma generation unit according to another embodiment of this disclosure.

FIG. 7 is a schematic cross-sectional view of the plasma generation unit 201 according to another embodiment of this disclosure. As shown in FIG. 7, the plasma generation unit 201 of this embodiment is similar to the plasma generation unit 200 of FIG. 6, and the main difference between the two is that, in this embodiment, the first electrode 210 is disposed above the second electrode 220.

Figure 8:
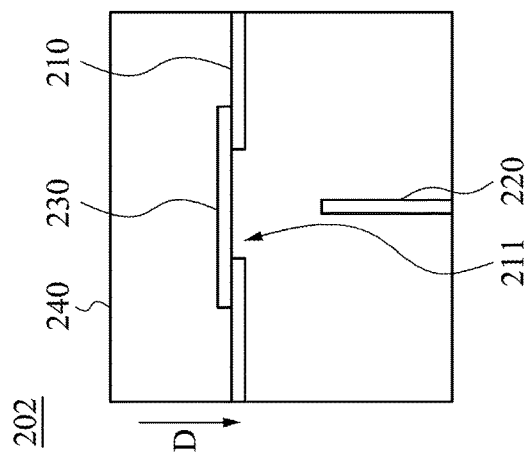
FIG. 8 is a schematic cross-sectional view of the plasma generation unit according to another embodiment of this disclosure.

FIG. 8 is a schematic cross-sectional view of the plasma generation unit 202 according to another embodiment of this disclosure. As shown in FIG. 8, the plasma generation unit 202 of this embodiment is similar to the plasma generation unit 201 of FIG. 7, and the main difference between the two is that, in this embodiment, the liquid-absorbing member 230 is disposed on one side of the first electrode 210 opposite to the second electrode 220, and the first electrode 210 has an second opening 211 to expose the liquid-absorbing member 230 to the second electrode 220. The second electrode 220 may be a pin.

Additionally, the second electrode 220 is not disposed directly above the liquid-absorbing member 230. When plasma is generated from the liquid-absorbing member 230, the temperature of the liquid-absorbing member 230 will rise, and evaporated liquid induces a convective flow of the fluid between the first electrode 210 and the second electrode 220. This may affect the stability of the light emitted by plasma. Because the second electrode 220 is not disposed directly above the liquid-absorbing member 230, the convective flow induced by the evaporated liquid has smaller influence on the fluid between the first electrode 210 and the second electrode 220, and the evaporated liquid will have smaller influence on the stability of the light emitted by plasma.

Figure 9:
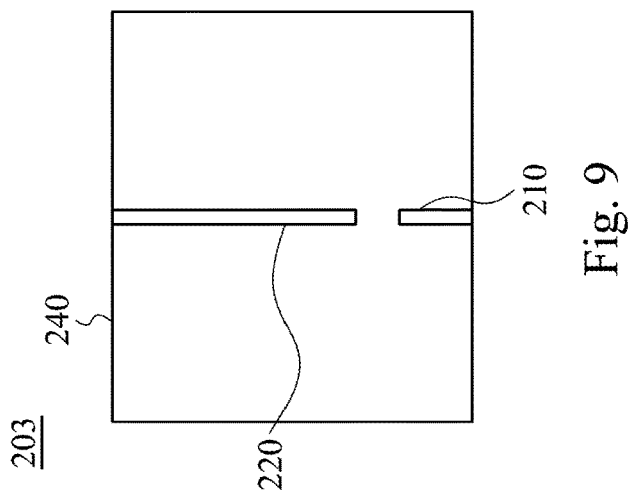
FIG. 9 is a schematic cross-sectional view of the plasma generation unit according to another embodiment of this disclosure.

FIG. 9 is a schematic cross-sectional view of the plasma generation unit 203 according to another embodiment of this disclosure. As shown in FIG. 9, the plasma generation unit 203 of this embodiment is similar to the plasma generation unit 200 of FIG. 6, and the main differences between the two are described below.

The plasma generation unit 203 does not include the liquid-absorbing member 230. The plasma generation unit housing 240 forms a space. The first electrode 210 and the second electrode 220 are disposed in the space, and the sample is the air in the space.

In some embodiment, the space is not a hermetic space, i.e., an open space connected to the external space. Embodiments of this disclosure are not limited thereto. In some other embodiments, the space is a hermetic space.

In some embodiments, the distance between the first electrode 210 and second electrode 220 is in a range from about 0.1 mm to about 1 mm. Alternatively, the distance between the first electrode 210 and second electrode 220 is about 0.5 mm. The end surface of the first electrode 210 is in a range from about 0.1 cm$^2$ to about 5 cm$^2$, and the end surface of the second electrode 220 is in a range from about 0.1 cm$^2$ to about 5 cm$^2$. Alternatively, the end surface of the first electrode 210 is about 0.32 cm$^2$, and the end surface of the second electrode 220 is about 0.32 cm$^2$.

Figure 10:
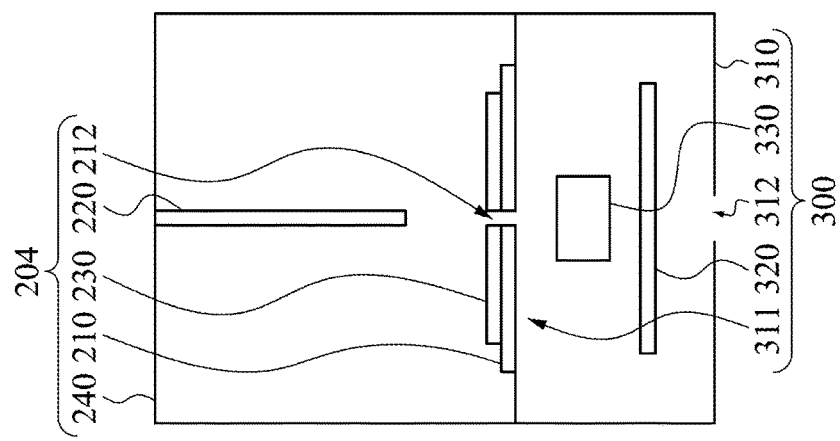
FIG. 10 is a schematic cross-sectional view of the plasma generation unit and the light decomposing unit according to another embodiment of this disclosure.

FIG. 10 is a schematic cross-sectional view of the plasma generation unit 204 and the light decomposing unit 300 according to another embodiment of this disclosure. As shown in FIG. 10, the first electrode 210 has an third opening 212, and the third opening 212 may be a slit or a pinhole. The light decomposing unit 300 includes a light decomposing unit housing 310 and a light dispersive member 320. The light decomposing unit housing 310 has a fourth opening 311 and a fifth opening 312. The fourth opening 311 receives the light emitted by the plasma. The light dispersive member 320 decomposes the light emitted by the plasma. The decomposed light can leave the light decomposing unit housing 310 through the fifth opening 312. Embodiments of this disclosure are not limited thereto. In some embodiments, the fourth opening 311 may be replaced by a transparent portion, and the fifth opening 312 may be replaced by a transparent portion. The transparent portions may be made of, for example, glass.

The light generated by the plasma passes through the third opening 212, and the light passing the third opening 212 becomes the light source of the light decomposing unit 300. Since the plasma is generated adjacent to the first electrode 210, so the light emitted by the plasma directly pass through the third opening 212 of the first electrode 210. Therefore, issues related to alignment can be avoided, such that the detection sensitivity can be enhanced. In addition, since the third opening 212 of the first electrode 210 controls the optical path as well, the overall configuration of the detection device 100 will become simpler, such that the size of the detection device 100 can be smaller.

The light decomposing unit 300 may further include a lens set 330. The lens set includes at least one lens, and the lens may be a convex lens, a concave lens, a plane convex lens, or a plane concave lens. The lens set 330 can adjust the light path of the light emitted by the plasma, or the lens set 330 can focus the light emitted by the plasma. Therefore, the space needed for the light path of the light emitted by the plasma can be reduced, and the size of the light decomposing unit 300 can be further reduced.

In some embodiments, the lens set 330 is disposed between the fourth opening 311 and the light dispersive member 320. In some embodiments, the lens set 330 is disposed between the light dispersive member 320 and the fifth opening 312. In some embodiments, the lens set 330 is disposed between the fourth opening 311 and the light dispersive member 320 and between the light dispersive member 320 and the fifth opening 312.

In some embodiments, the dimension (for example, the width or the diameter) of the third opening 212 may be in a range from about 0.01 mm to about 2 mm. When the third opening 212 is a pinhole, the diameter of the third opening 212 may be in a range from about 0.01 mm to about 2 mm. When the third opening 212 is a slit, the width of the third opening 212 may be in a range from about 0.01 mm to about 2 mm. The shape of the third opening 212 may be a circle, a rectangle, an ellipse, or a triangle. Embodiments of this disclosure are not limited thereto. The person having ordinary skill in the art can make proper modifications to the third opening 212 depending on the actual application.

The light dispersive member 320 may be a prism or a grating. Embodiments of this disclosure are not limited thereto. The person having ordinary skill in the art can make proper modifications to the lightdispersive member 320 on the actual application.

After the light is decomposed by the light dispersive member 320, different components of the light with different wavelengths will go in different directions. Then, different components of the light with different wavelengths image in different positions of the sensor of the image capturing unit 910. Therefore, by measuring the brightnesses of different positions of the image formed by the image capturing unit 910, the spectrum of the light emitted by the plasma of the sample can be known.

Figure 11:
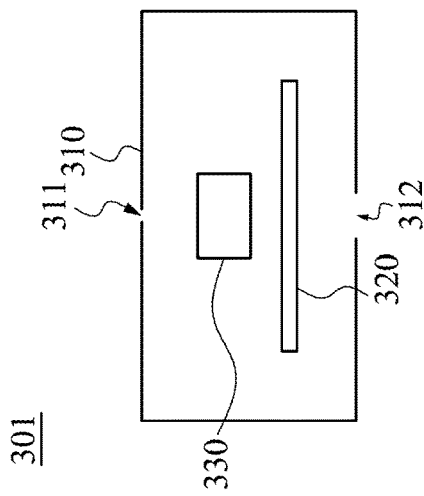
FIG. 11 is a schematic cross-sectional view of the light decomposing unit according to another embodiment of this disclosure.

FIG. 11 is a schematic cross-sectional view of the light decomposing unit 301 according to another embodiment of this disclosure. As shown in FIG. 11, the light decomposing unit 301 of this embodiment is similar to the light decomposing unit 300 of FIG. 10, and the main differences between the two are described below.

The fourth opening 311 is a pinhole or a slit, and the first electrode 210 (see FIG. 10) does not have third opening 212 (see FIG. 10) in this embodiment. The light generated by the plasma will pass the fourth opening 311, and the light passing through the fourth opening 311 will become the light source of the light decomposing unit 300.

In some embodiment, the dimension (for example, the width or the diameter) of the fourth opening 311 may be in a range from about 0.01 mm to about 2 mm. When the fourth opening 311 is a pinhole, the diameter of the fourth opening 311 may be in a range from about 0.01 mm to about 2 mm. When the fourth opening 311 is a slit, the width of the fourth opening 311 may be in a range from about 0.01 mm to about 2 mm. The shape of the fourth opening 311 may be a circle, a rectangle, an ellipse, or a triangle. Embodiments of this disclosure are not limited thereto. The person having ordinary skill in the art can make proper modifications to the fourth opening 311 depending on the actual application.

Figure 12:
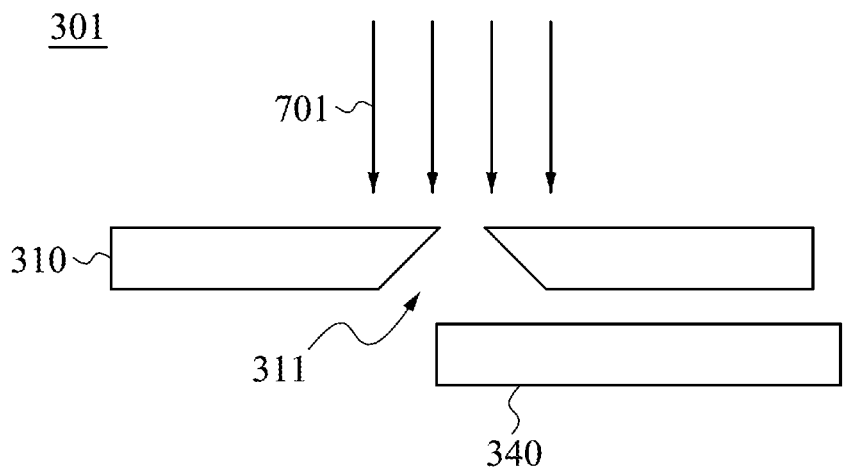
FIG. 12 is a partially enlarged view of the light decomposing unit according to another embodiment of this disclosure.

FIG. 12 is a partially enlarged view of the light decomposing unit 301 according to another embodiment of this disclosure. As shown in FIG. 12, the light decomposing unit 301 further includes a light blocking structure 340. The light blocking structure 340 blocks a zeroth order diffraction part of light 701 passing the fourth opening 311.

Since the light passes the fourth opening 311, and the image capturing unit 910 of the mobile electronic device 900 receives the light decomposed by the light decomposing unit 301, there will be a zeroth order diffraction part of the light images on the image capturing unit 910. The brightness of the zeroth order diffraction part of the light is much greater than the brightness of the other part of the light. If the image capturing unit 910 changes the exposure time and the aperture according to the maximum brightness of the incident light, the other part of the light, which includes necessary spectrum information, will become unclear in the detected image. If the light blocking structure 340 blocks the zeroth order diffraction part of light 701 passing the fourth opening 311, the zeroth order diffraction part of light 701 will not affect the exposure time and the aperture of the image capturing unit 910, and the other part of the light will not become unclear in the detected image.

Figure 13:
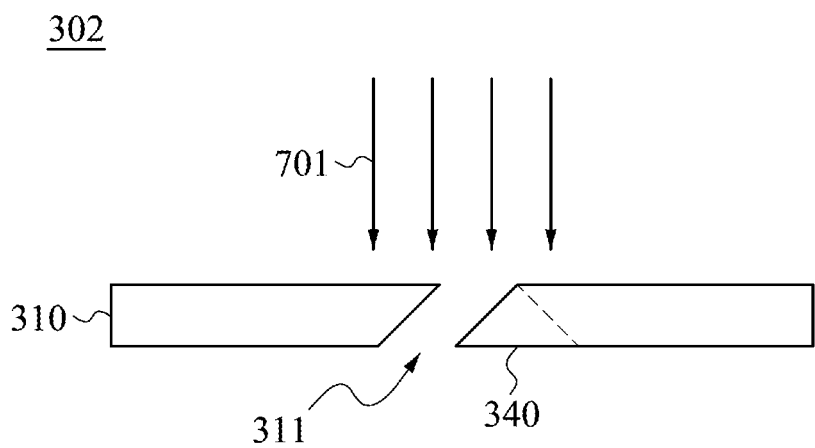
FIG. 13 is a partially enlarged view of the light decomposing unit according to another embodiment of this disclosure.

FIG. 13 is a partially enlarged view of the light decomposing unit 300 according to another embodiment of this disclosure. As shown in FIG. 13, the light decomposing unit 302 of this embodiment is similar to the light decomposing unit 301 of FIG. 12, and the difference between the two is that, in this embodiment, the light blocking structure 340 is integrally formed on the light decomposing unit housing 310.

In some embodiments, the light blocking structure 340 may be integrally formed on the first electrode 210 to form a structure similar to the structure of FIG. 13.

Reference is made back to FIG. 2. The detection device 100 further includes a switch control unit 500. The switch control unit 500 controls the time period between the turn-on time of the plasma generation unit 200 and the turn-on time of the image capturing unit 910 of the mobile electronic device 900. In some embodiments, the time period is zero second. In other words, the switch control unit 500 turns on the plasma generation unit 200 and the image capturing unit 910 of the mobile electronic device 900 simultaneously. Then, after the plasma generation unit 200 is turned on, the plasma is generated from the sample, and the light emitted by the plasma is then decomposed by the light decomposing unit 300. Since the image capturing unit 910 is turned on at the same time, the decomposed light images on the sensor of the image capturing unit 910.

Embodiments of this disclosure are not limited thereto. The time period may be in a range from about 0.001 second to 1 second. In some embodiments, the time period is 0.01 second. In other words, the plasma generation unit 200 is turned on first, and then the light decomposing unit 300 is turned on.

The switch control unit 500 may include a switch to turn on the plasma generation unit 200. When the user turns on the image capturing unit 910 of the mobile electronic device 900 by the user interface of the mobile electronic device 900, the mobile electronic device 900 transmits a signal to the switch, and the switch of the switch control unit 500 turns on the plasma generation unit 200. Therefore, the switch control unit 500 turns on the plasma generation unit 200 and the image capturing unit 910 of the mobile electronic device 900 simultaneously.

The switch may be a light-sensitive switch, and the switch may be triggered by the light source of the mobile electronic device 900. In some embodiments, the switch may be triggered by the flash lamp of the mobile electronic device 900. Embodiments of this disclosure are not limited thereto. In some other embodiments, the switch may be disposed in front of the display screen, and the switch is triggered by the light emitted by the display screen.

The switch may be a transistor, an electronic chip, an on/off switch, and the switch control unit 500 may further include a signal transmitting module. The signal transmitting module may be a wire, and the mobile electronic device 900 can transmit a current signal through the headphone jack of the mobile electronic device 900 and the wire to the switch to turn on the plasma generation unit 200. Alternatively, the signal transmitting module may be a bluetooth module. The mobile electronic device 900 can transmits an electromagnetic signal to the bluetooth module, and then the bluetooth module transmits a signal to the switch to turn on the plasma generation unit 200.

In some embodiments, in order to tailor the properties, such as the conductivity, the pH value, or the chemical composition, the detection device 100 may further include a third electrode (not shown in Figs.) and a fourth electrode (not shown in Figs.). The third electrode and the fourth electrode form a set of electrodes. The detection device 100 cooperated with the mobile electronic device 900 detects whether an element exists in the sample by spectral analysis of the plasma generated from the sample, so the detection device 100 can detect a variety of kinds of elements with high sensitivity. In addition, since the detection device 100 is used with the mobile electronic device 900, the detection device 100 does not need to include the image capturing unit 910 and the data processing unit 920. Therefore, the manufacturing cost of the detection device 100 can be reduced. Finally, the plasma generation unit 200 and the light decomposing unit 300 can be manufactured in small sizes, so the detection device 100 is portable. Therefore, it is very convenient to detect whether an element exists in the sample by using the detection device 100.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C. § 112, 6th paragraph. In particular, the use of "step of" in the claims herein is not intended to invoke the provisions of 35 U.S.C. § 112, 6th paragraph.

What is claimed is:

1. A spectral analysis device which cooperates with an external mobile electronic device having an image capturing sensor and a data processor, the spectral analysis device comprising:
   a plasma generator configured to generate plasma from a sample; and
   a light decomposer configured to decompose light emitted by the plasma for spectral analysis, wherein the light decomposed by the light decomposer is received directly and analyzed by the image capturing sensor and the data processor of the external mobile electronic device to determine whether an element exists in the sample.

2. The spectral analysis device of claim 1, further comprising:
a fixing member configured to fix the spectral analysis device to the external mobile electronic device.

3. The spectral analysis device of claim 1, wherein the plasma generator comprises a first electrode and a second electrode, and the sample is located between the first electrode and the second electrode.

4. The spectral analysis device of claim 3, wherein the plasma generator further comprises:
a plasma generator housing forming a space, wherein the first electrode and the second electrode are disposed in the space, and the sample is an air in the space.

5. The spectral analysis device of claim 3, wherein the plasma generator further comprise a liquid-absorbing member, the liquid-absorbing member is disposed on the first electrode, and the sample is a liquid in the liquid-absorbing member.

6. The spectral analysis device of claim 5, wherein the second electrode is disposed above the first electrode.

7. The spectral analysis device of claim 5, wherein the first electrode is disposed above the second electrode.

8. The spectral analysis device of claim 5, wherein the liquid-absorbing member is made of a filter paper, a fabric, or a porous material.

9. The spectral analysis device of claim 5, wherein the liquid-absorbing member is attached to the first electrode, and the first electrode is a negative electrode.

10. The spectral analysis device of claim 3, wherein the first electrode has an opening, and the opening is a slit or a pinhole.

11. The spectral analysis device of claim 3, wherein the second electrode is a pin.

12. The spectral analysis device of claim 1, wherein the plasma generator comprises a first electrode, a second electrode, and a liquid-absorbing member, the liquid-absorbing member is disposed on the first electrode, the sample is a liquid in the liquid-absorbing member, and the second electrode is not disposed directly above the liquid-absorbing member.

13. The spectral analysis device of claim 1, wherein the light decomposer comprises a light dispersive member configured to decompose the light emitted by the plasma.

14. The spectral analysis device of claim 13, wherein the light dispersive member is a prism or a grating.

15. The spectral analysis device of claim 1, wherein the light decomposer comprises a light decomposer housing, and the light decomposer housing has an opening configured to receive the light emitted by the plasma.

16. The spectral analysis device of claim 15, wherein the opening is a pinhole or a slit.

17. The spectral analysis device of claim 15, wherein the light decomposer further comprises a light blocking structure configured to block a zeroth order diffraction part of light passing the opening.

18. The spectral analysis device of claim 17, wherein the light blocking structure is integrally formed on the light decomposer housing.

19. The spectral analysis device of claim 1, further comprising:
a switch control unit configured to control a time period between a turn-on time of the plasma generator and a turn-on time of the image capturing sensor of the external mobile electronic device,
wherein the switch control unit comprises a switch configured to turn on the plasma generator, and the switch of the switch control unit turns on the plasma generator in response to an operation of the external mobile electronic device.

20. The spectral analysis device of claim 1, wherein the external mobile electronic device is sold or purchased separately from the spectral analysis device.

* * * * *